(12) United States Patent
Delogé et al.

(10) Patent No.: US 6,746,453 B2
(45) Date of Patent: Jun. 8, 2004

(54) TARGETING APPARATUS FOR USE IN PERFORMING TRANSFEMORAL OSTEOTOMY

(75) Inventors: Nicolas Delogé, Douvres (FR); Jean-Pierre Brée, Fontaine Etoupefour (FR); Arnaud Aux Epaules, Saint-aubin-sur-mer (FR); Philippe Lavieille, Caen (FR); Christophe Cueille, Missy (FR)

(73) Assignee: Benoist Girard SAS (FR)

( * ) Notice: Subject to any disclaimer, the term of this patent is extended or adjusted under 35 U.S.C. 154(b) by 59 days.

(21) Appl. No.: 10/011,047

(22) Filed: Nov. 8, 2001

(65) Prior Publication Data

US 2002/0095159 A1 Jul. 18, 2002

(30) Foreign Application Priority Data

Nov. 13, 2000 (GB) .............................. 00 27698
Mar. 8, 2001 (GB) .............................. 01 05779

(51) Int. Cl.[7] .............................. A61B 17/58; A61F 2/38
(52) U.S. Cl. ...................... 606/98; 623/20.35
(58) Field of Search .............................. 606/96, 89, 53, 606/54, 59, 86, 102, 104, 99, 98; 123/20.35, 23.27, 908

(56) References Cited

U.S. PATENT DOCUMENTS

| 2,362,957 A | | 9/1944 | Hackett |
|---|---|---|---|
| 3,945,377 A | | 3/1976 | Kronner |
| 4,037,592 A | * | 7/1977 | Kronner ...................... 606/97 |
| 4,187,840 A | | 2/1980 | Watanabe |
| 4,541,424 A | | 9/1985 | Grosse et al. |
| 4,667,664 A | | 5/1987 | Taylor et al. |
| 4,865,025 A | | 9/1989 | Buzzi et al. |
| 4,881,535 A | | 11/1989 | Sohngen |
| 4,883,048 A | | 11/1989 | Purnell et al. |
| 4,911,153 A | | 3/1990 | Border |
| 5,078,719 A | | 1/1992 | Schreiber |
| 5,176,681 A | | 1/1993 | Lawes et al. |
| 5,207,682 A | | 5/1993 | Cripe |
| 5,306,278 A | | 4/1994 | Dahl et al. |
| 5,334,192 A | | 8/1994 | Behrens |
| 5,374,271 A | | 12/1994 | Hwang |
| 5,403,322 A | * | 4/1995 | Herzenberg et al. .......... 606/98 |
| 5,431,657 A | | 7/1995 | Rohr |
| 5,620,449 A | | 4/1997 | Faccioli et al. |
| 5,649,930 A | | 7/1997 | Kertzner |
| 5,665,086 A | * | 9/1997 | Itoman et al. ................. 606/64 |
| 6,027,506 A | * | 2/2000 | Faccioli et al. ............... 606/98 |
| 6,102,953 A | * | 8/2000 | Huebner ................. 623/19.11 |
| 6,168,628 B1 | * | 1/2001 | Huebner ................. 623/19.11 |
| 6,494,913 B1 | * | 12/2002 | Huebner ................. 623/19.11 |
| 2002/0133172 A1 | | 9/2002 | Lambrecht et al. |

FOREIGN PATENT DOCUMENTS

| DE | 198 20 721 A1 | 4/1999 |
|---|---|---|
| DE | 299 22 792 U1 | 4/2000 |
| EP | 0 514 662 A | 4/1992 |
| FR | 2 692 472 | 12/1993 |
| FR | 2 789 570 | 12/1999 |

* cited by examiner

*Primary Examiner*—Eduardo C. Robert
*Assistant Examiner*—D. Austin Bonderer
(74) *Attorney, Agent, or Firm*—Lerner, David, Littenberg, Krumholz & Mentlik, LLP

(57) ABSTRACT

A targeting apparatus for use in performing transfemoral osteotomy surgery includes a support element provided with a drill guide. A device is provided for securing the support element to a prosthesis to be implanted, and to a resectioned femur. An adjusting device for adjusting the angular position of the drill guide in relation to the resectioned femur about a proximal-distal axis is also included.

29 Claims, 7 Drawing Sheets

TARGETING APPARATUS FOR USE IN PERFORMING TRANSFEMORAL OSTEOTOMY

BACKGROUND OF THE INVENTION

This invention relates to a targeting apparatus for use in performing transfemoral osteotomy. In this surgical technique the femur is exposed along a proximal-distal line, the soft tissue (skin, muscle) being folded back on each side to expose the bone. The proximal end of the femur is now opened as a "window" and a femoral prosthesis is inserted into the bone canal.

The technique requires careful pre-operative planning, usually from X-rays and it is possible to calculate in advance how far to cut the "window" so that the distal edge of the "window" end can become a datum base.

There are obvious difficulties in assessing the particular angular position of the prosthesis in the femoral canal and the exact location of the resectioning of the femur must be accurately judged. A further difficulty arises with regard to the placement of one or more retaining bolts towards the distal end of the stem of the prosthesis. These bolts or pins pass through the bone, the stem of the prosthesis and out through the other side of the bone thus anchoring the prosthesis in position. It is difficult for surgeons to judge the exact position to drill the holes in the bone to coincide with the holes in the implant and it is also necessary to select the correct angular position for the prosthesis and therefore the holes. It is also difficult to judge the exact distance down the femur for the holes to achieve the correct leg length of the correction.

The present invention is intended to overcome some of the difficulties referred to above and provide apparatus which provides a more accurate surgical technique.

SUMMARY OF THE INVENTION

According to the present invention, targeting apparatus for use in performing transfemoral osteotomy surgery comprises a support element provided with a drill guide, a connector for securing the support element to a prosthesis to be implanted, and to a resectioned femur, and a device for adjusting the angular position of the drill guide in relation to the resectioned femur about a proximal-distal axis.

Thus, the apparatus can be used to accurately locate the angular position of the drill guide and the prosthesis (anteversion setting) which can be used to drill the holes to take the retaining bolt or bolts in the bone. Preferably the support element includes means for connection to the proximal end of the femoral prosthesis. An indicator can be provided to indicate the angular position of the drill guide relative to the resectioned femur.

Thus, after careful X-ray examination the precise anteversion setting can be decided and this can then be transferred to the apparatus thus ensuring the correct angular position.

The apparatus can also include a device for adjusting the support element to accommodate alternative leg lengths. In order to do this an adjusting device can be included to vary the proximal-distal position of the support element in relation to the prosthesis securing means.

Once again, the necessary dimensions and requirements can be taken from X-rays and preset on the apparatus. With this arrangement the drill guide can be located at a predetermined proximal-distal position from the connector to the proximal end of the femoral prosthesis.

A locator can be included for locating the drill guide in alternative proximal-distal positions on the support element thus the apparatus can be adapted for prostheses with holes in different positions and two or more drill guides can be provided.

The connector for securing the support element to the resectioned femur is preferably in the form of an adjustable open jawed clamp adapted to partially surround the femur with which it is to be used.

A guide can be included for locating the support element on the resectioned proximal end of the femur and these guide means can be carried on the femur connector.

The support element can be in the form of an L-shaped frame, one arm of which carries the drill guide and the femur securing means and the other arm carrying the connector for connection to the femoral prosthesis which is to be implanted.

With this arrangement the femur connector can be connected to the L-shaped frame by a bracket which can be adjusted in proximal-distal directions on the frame and in relation to which the femur connector can be angularly adjusted about a proximal-distal axis.

In a preferred embodiment the bracket is readily removable from the L-shaped frame.

The femur connector can include a device for adjusting and clamping the connector according to the femur diameter.

In another preferred embodiment the connector for securing the support element to the resectioned femur includes a universal joint.

BRIEF DESCRIPTION OF THE DRAWINGS

The invention can be performed in many ways but one embodiment will now be described by way of example and with reference to the accompanying drawings in which.

DETAILED DESCRIPTION OF THE PREFERRED EMBODIMENTS

Figure 1:
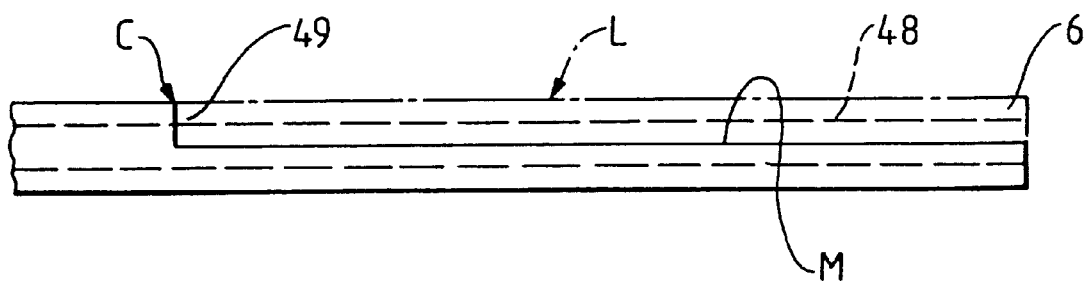
FIG. 1 is a diagrammatic side view of a femur showing how it is cut for performing transfemoral osteotomy surgery.
Figure 2:
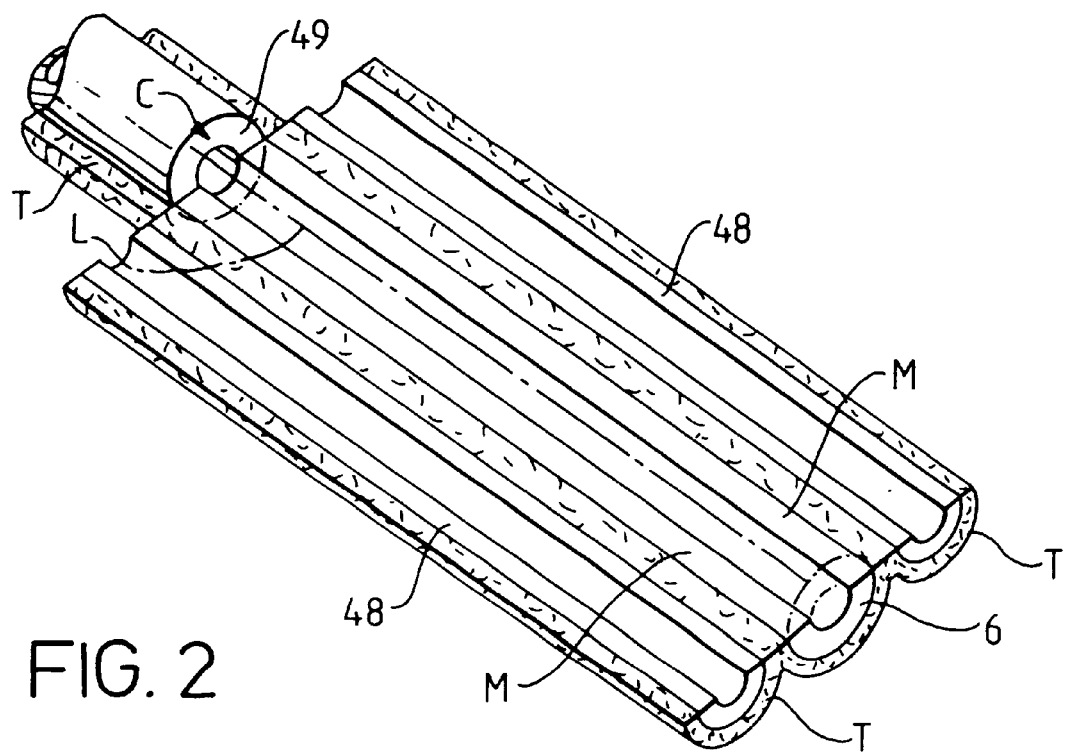
FIG. 2 is a diagrammatic perspective view showing how the "window" is formed in the femur for transfemoral osteotomy surgery.

FIGS. 1 and 2 show, in simplified form, how transfemoral osteotomy surgery is performed. The soft tissue indicated by reference letter T in FIG. 2 is exposed along a proximal/distal line indicated by broken line L in FIG. 2. The soft tissue T is folded back on each side to expose the femur 6 and the bone is resected with three cuts along the same line L two side cuts M and with a transverse cut C. The proximal end of the femur is now opened, as shown in FIG. 2, as a "window". From FIG. 2 it will be seen that an upper quarter 48 is now laid on each side of the remaining part of the bone to expose the bone canal into which the prosthesis is to be inserted.

As shown in FIGS. 3 to 6 the preferred instrument of the apparatus present invention for performing transfemoral osteotomy surgery comprises a support element 1 provided with two drill guides 2, a connector 3 for securing the support element 1 to a prosthesis 4 which is to be implanted and connector or clamp 5 for securing the support element 1 to a resectioned femur which is indicated by reference numeral 6. An adjuster 7 is included for adjusting the angular position of the drill guides 2 in relation to the resectioned femur 6 about a proximal-distal axis.

The support element 1 is in the form of an L-shaped frame having a first arm 10 and a second arm 11. First arm 10 carries drill guides 2 and femur connector 5 and second arm 11 carries the connector 3 for connecting support 1 to the proximal end of the femoral prosthesis 4.

Femur connector or clamp 5 (to be described below) is connected to first arm 10 by an adjustable bracket 12 which can be adjusted in proximal-distal directions only in a slot 13 in arm 10 and locked in position by a retaining nut 14, and femur connector or clamp 5 can be angularly adjusted in relation to the bracket 12 in a slot 15 provided on the bracket and locked in position by a nut 16. Nut 16 is carried on a screw threaded boss indicated by reference numeral 17 which is carried on femur connector 5.

Figure 4:
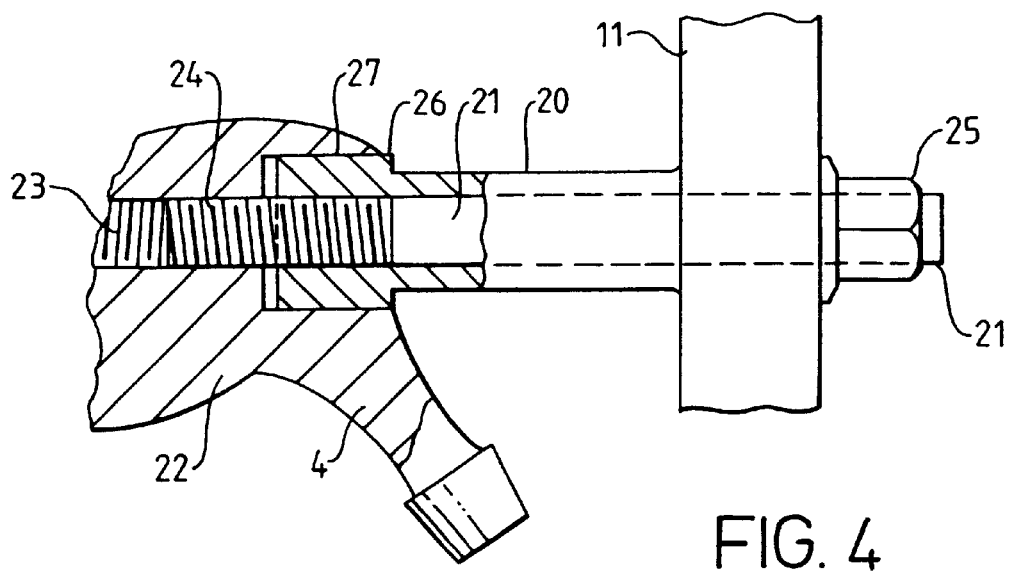
FIG. 4 is a part cross-sectional view of a connector for securing the element of the apparatus shown in FIG. 3 to a prosthesis to be implanted.

Connector 3 for connecting the support element 1 to the femoral prosthesis which is to be implanted is shown in more detail in FIG. 4 and comprises a sleeve 20 secured to second arm 11 and in which is located a securing stud 21.

The proximal end 22 of prosthesis 4 is provided with a screw threaded bore 23 in which a screw threaded portion 24 of stud 21 can be located. The other end of the stud is held by a nut 25.

The distal end of sleeve 20 is provided with a pair of opposed projecting keys 26 which engage in keyways 27 in the form of slots provided in an enlarged end portion of bore 23.

Thus, it will be seen that prosthesis 4 can be held in position on arm 11 and is restrained against relative rotation by the keys 26 and keyways 27.

Figure 5:
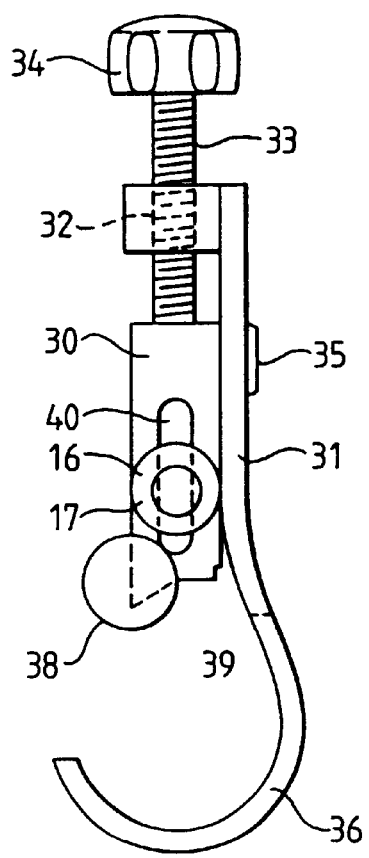
FIG. 5 is a side elevation of a clamp shown in FIG. 3 for securing the support element to a resectioned femur.
Figure 6:
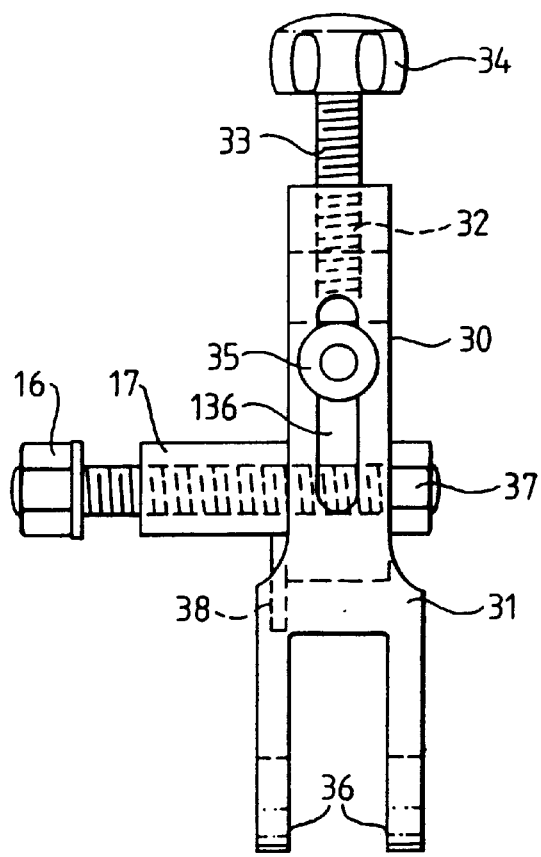
FIG. 6 is a front elevation of the clamp device shown in FIG. 5.

The preferred connector 5 for connecting the support element to resectioned femur 6 is most clearly shown in FIGS. 5 and 6 and comprises an open-jawed clamp device. This device has a main body portion 30 on which is located a movable clamping jaw 31. The upper part of the clamping jaw 31 has a screw threaded bore 32 which houses a threaded member 33 one end of which carries an operating handle 34 and the other end of which is rotatably housed in the body 30. Thus, rotation of the handle 34 raises and lowers the clamp 31 which is also located by a retaining screw 35 which passes through a slot 136.

The lower end of the open jawed clamp is formed as a pair of curved tines 36 which are adapted to extend around the resectioned femur to which the device is to be clamped.

In the preferred embodiment a guide in the form of a disc 38 mounted on body 30 is provided, the disc projecting below the lower end 39 of body 30.

Boss 17 is located in a slot 40 in body 30 and held by a nut 37 but is free to move so that the position of the clamp adjusts itself in relation to the adjustment bracket 12 to alter the radial distance from femur 6.

In the preferred embodiment drill guides 2 are carried on arm 10 by a clamping plate 40 which is held in place by a screw threaded shaft 41 retained by a nut 42. Shaft 41 passes through one of a series of four openings 43 in arm 1. As will be seen, once the guides have been fixed in position there is a predetermined distance from the guides to the connector 3 for connecting support element 1 to femoral prosthesis 4. This distance can however be adjusted by using the alternative openings 43. Drill guides 2 are set for a position with respect to the given prosthesis so that they are fixed and aligned with the holes 44 in prosthesis 4.

A typical drill bit 45 is shown in place in one of drill guides 2 and its lower operative end 46 indicates how it has been drilled through the femur 6 passing through the existing holes 44 in the stem 47 and through the other side of femur 6.

Figure 3:
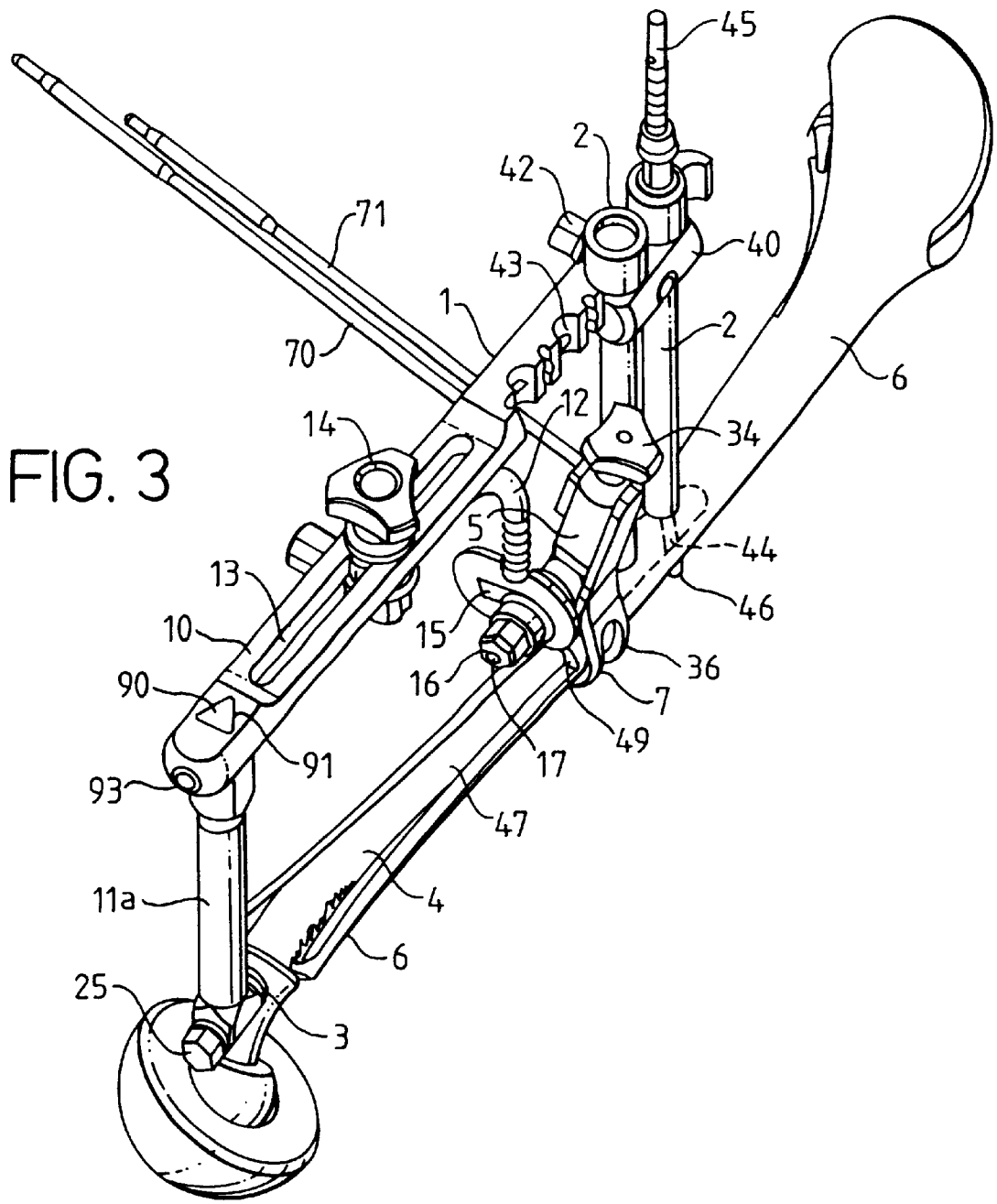
FIG. 3 is a diagrammatic isometric view of apparatus according to the invention.

As shown in FIG. 3 second arm 11 can be arranged to be detachable from the support element 1 and is secured to the arm 10 by a plug and socket connection indicated by reference numeral 90. A triangular socket 91 is provided in arm 10 into which a triangular shaped plug on arm 11 is inserted. The plug 92 is retained in position by a locking screw 93 in the end of the arm.

In FIG. 3 the bone and soft tissue T (not shown), which has been folded back to provide the "window" and expose femur 6.

To carry out the surgery relating to a transfemoral osteotomy the surgeon first ensures that appropriate X-rays have been taken so that he can consider the amount of bone which needs to be removed from the femur. Once having decided this the measurements are carefully taken for further use with the apparatus according to the invention.

The "window" is now opened to reveal the femur and the bone is cut appropriately to provide a proximal end C, indicated by reference numeral 49 in FIG. 3. The connector or clamp 5 is now located in position on the femur by tucking it around the femur and ensuring that the guide disc 38 is close up against the severed end 49. The positioning is achieved with a rotative movement. Once in place the handle 34 is operated to close the clamp and retain it in place. The stem 47 of the prosthesis 4 is now inserted in the femoral canal and the frame in the form of the arms 10 and 11 is connected to it by means of connector 3.

The nut 14 is released to allow the bracket 12 to move in the slot 13 and so that it can be secured to the femur connector 5 by boss 17 and nut 16 through slot 15. The release of the nut 16 allows slot 15 to be placed on boss 17 at the appropriate radial distance from the femur prior to subsequent tightening. It will be appreciated that the proximal-distal movement in slot 13 accommodates the leg length adjustment. The ante/retroversion (version angle) adjustment is now carried out by revolving the frame about the axis of prosthesis 4 and the particular angle adjustment is set by tightening nut 16. During this angular movement the prosthesis 4 which is securely attached to the support frame revolves with it as do drill guides 2.

The proximal-distal positioning of the drill guides is set according to the pre-operative planning and they are now positioned by releasing the nut 42 so that they can be located in contact with the cortex of the femur and the nut suitably tightened.

The drill guides can now be used to produce the necessary holes through the bone to accept the required bolts or pins.

In the arrangement described above two drill guides are shown but only one or any other number can be utilized if required.

The apparatus can be simply removed by releasing the stud 21 in the prosthesis 4, releasing the nut 16 and removing the frame. The clamp 6 can be removed separately.

The "window" is now closed according to any known post-operative technique.

Figure 7:
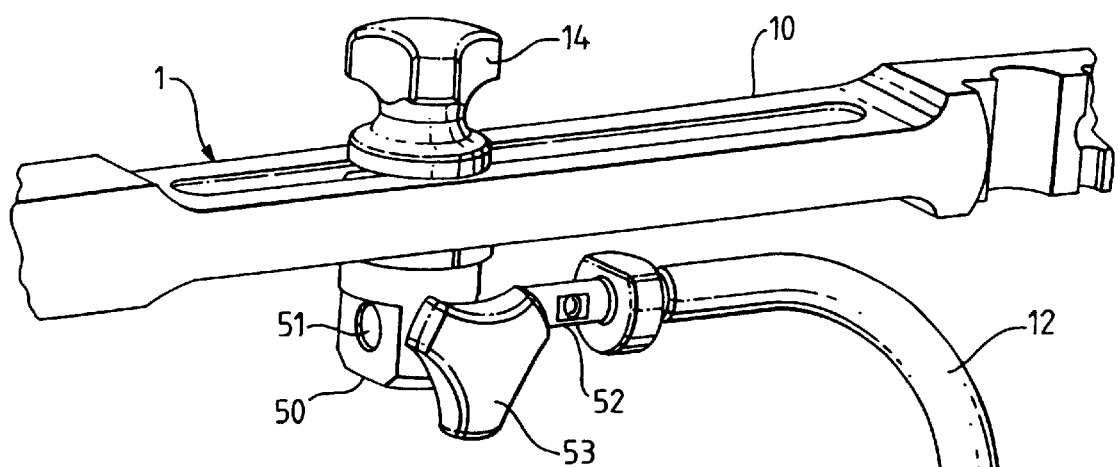
FIG. 7 is an isometric view of part of the support element.

FIG. 7 shows an alternative embodiment in which the same reference numerals are used to indicate similar parts. In this arrangement the adjustable bracket 12 can be readily disconnected from the first arm 10 of the L-shaped frame. In this embodiment nut 14 is shown as a hand nut and is carried on a boss 50 which has a bore 51 adapted to receive a spigot or trunnion 52 provided on the end of the bracket 12. Boss 50 also carries a screw threaded locking nut 53 which can be advanced through a screw threaded bore (not shown) so that it engages against the spigot 52 where it is located in the bore 51 to clamp it in position. This embodiment enables disconnection of the assembly without having to unscrew locking nut 14 thus enabling the leg length to be set without readjustment.

Figure 8:
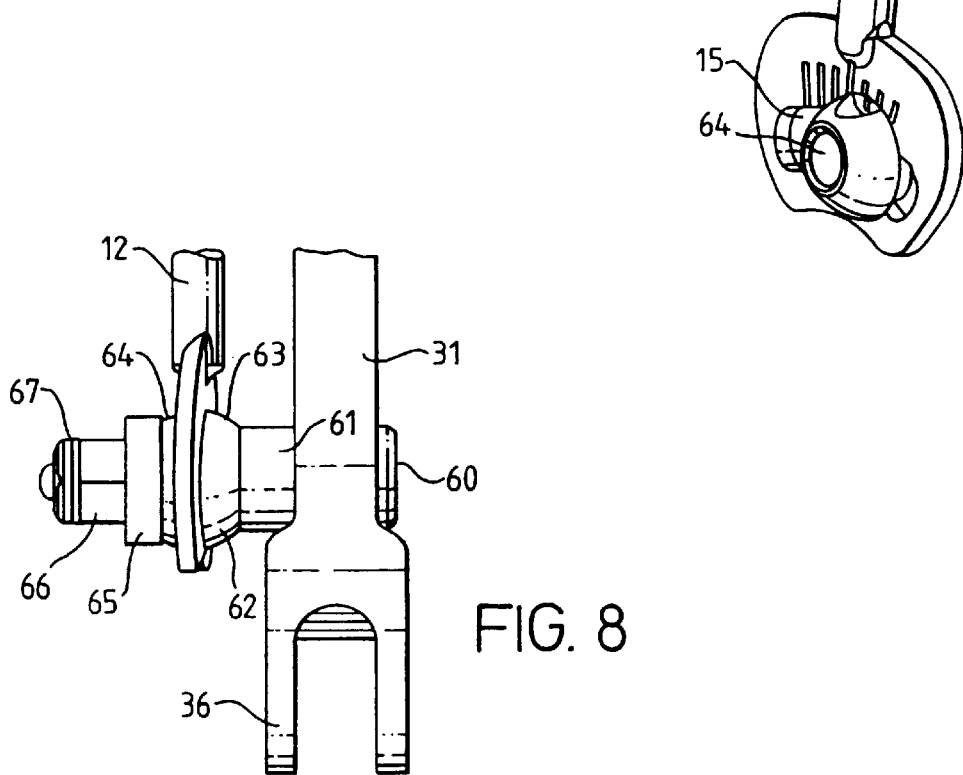
FIG. 8 is a partial side view of an alternative construction of the clamp shown in FIGS. 5 and 6.
Figure 9:
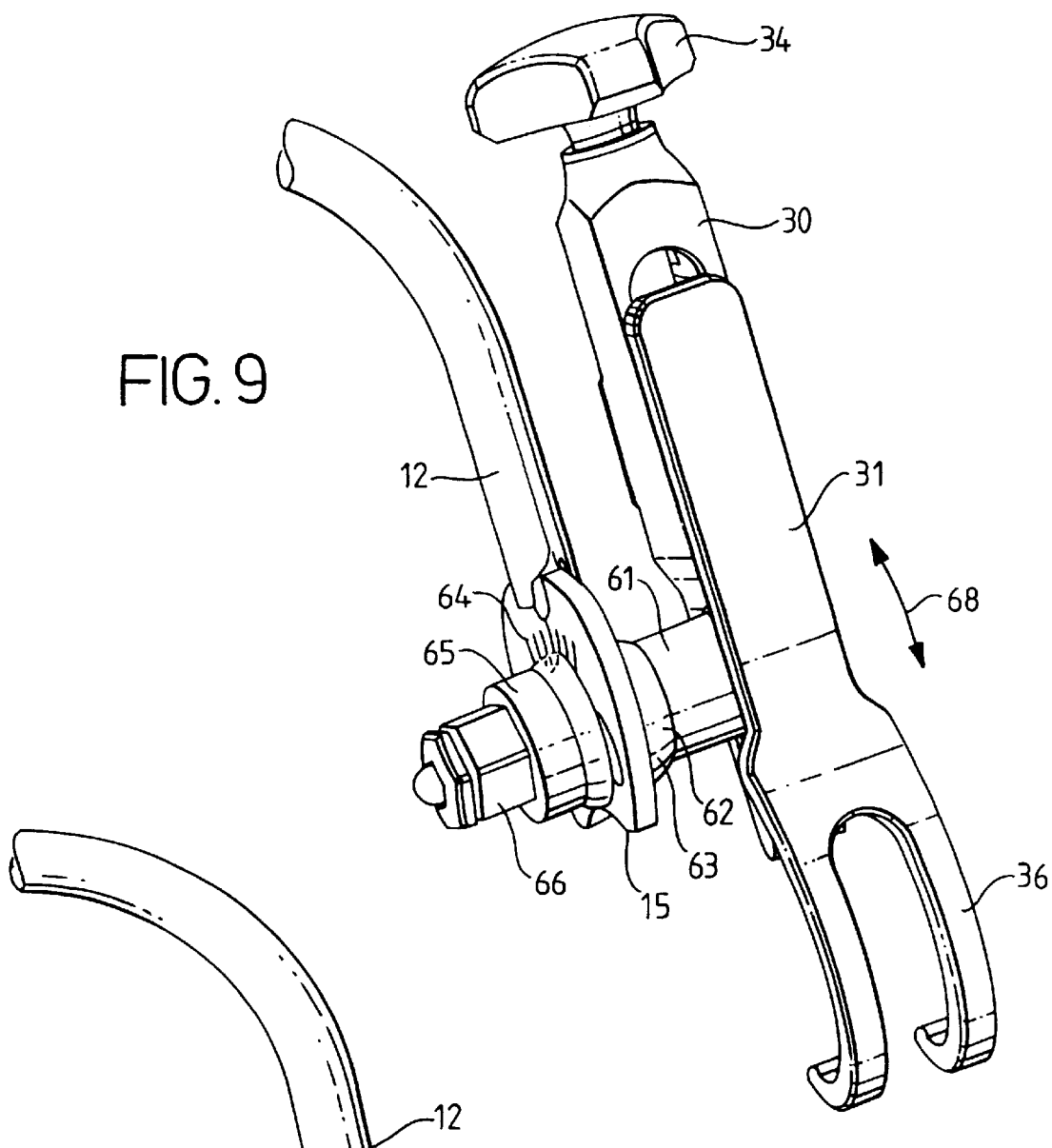
FIG. 9 is an isometric view of the embodiment shown in FIG. 8.
Figure 10:
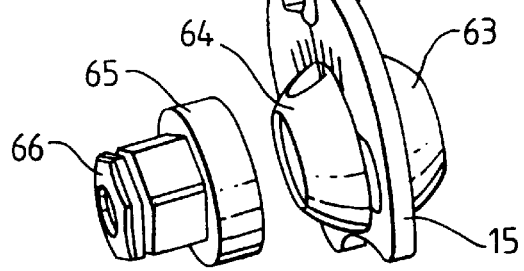
FIG. 10 is an isometric view of the embodiment shown in FIG. 9 partially dissembled.

FIGS. 8, 9 and 10 shown an alternative embodiment for the open jawed clamp device and the same reference numerals are used to indicate similar parts to those shown in FIGS. 5 and 6. In this embodiment however, boss 17 is replaced by a bolt 60 which extends through slot 40 and carries a spacer 61. One end 62 of spacer 61 is dished to accommodate a part-spherically shaped washer 63. A second part spherically-shaped washer 64 is also located on the screw 60 and one side of this is housed in a dished portion 65 of a nut 66. The nut 66 has a circumferential groove 67 to accommodate resilient ring (not shown) which can act to retain a socket wrench during assembly. Each of the washers 64 and 63 also has a flat side which are located against the sides of slot 15 on bracket 12 when the whole construction is assembled together with the screw 60 passing through slot 15.

With the nut 66 tightened the assembly is tightly clamped together but if nut 66 is slackened bracket 12 can align itself in three different directions by movement of the part spherical washers in the spacers 61 and 65. This enable three relative rotations, one of which is the anteversion setting and the other two rotations enable centering of the stem in the femur if the clamp is ill positioned on it.

As the attachment of clamping jaw 31 to the bracket 12 is also adjustable and can be clamped in position after movement of the clamp in the direction of the arrows 68 on FIG. 9 this enables the automatic adoption of the femur diameter and once set, can be tightly adjusted to provide rigidity of the assembly.

Figure 11:
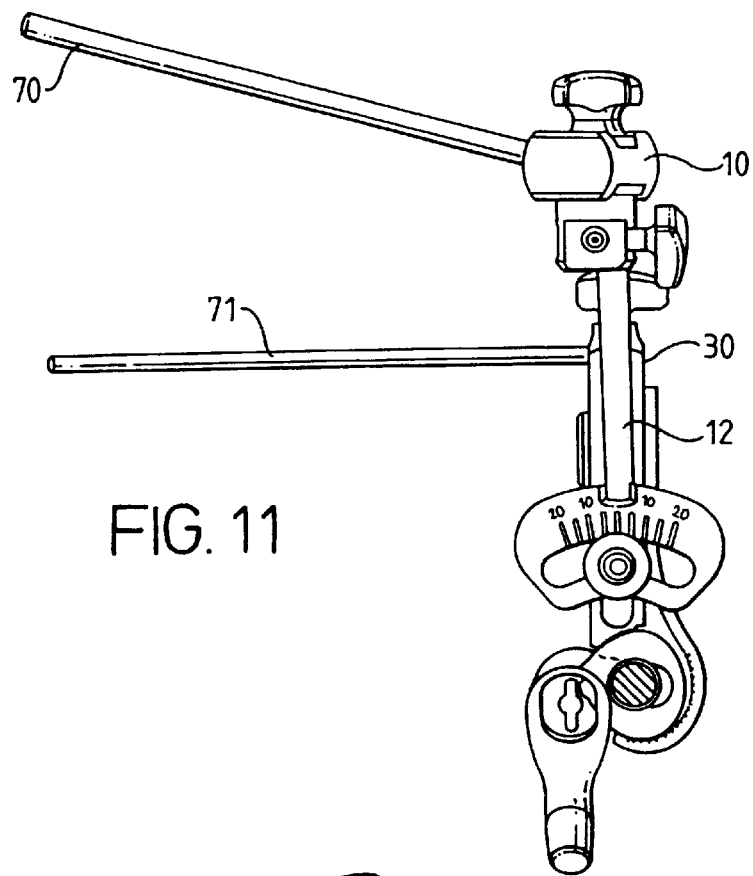
FIG. 11 is an end view of the device shown in FIG. 3 incorporating the alternative embodiments shown in FIGS. 7, 8, 9 and 10 and including visual indicator guides and with the support element in a first position.

FIG. 11 shows how visual indicator guides can be provided. Thus, a visual indicator guide arm 70 is attached to the L-shaped frame 10 in the form of a rod which extends at 15° to the axis of the first arm 10. A second indicator guide 71 which is also in the form of a rod is attached at an angle normal to the longitudinal axis of the clamp main body portion 30.

Figure 12:
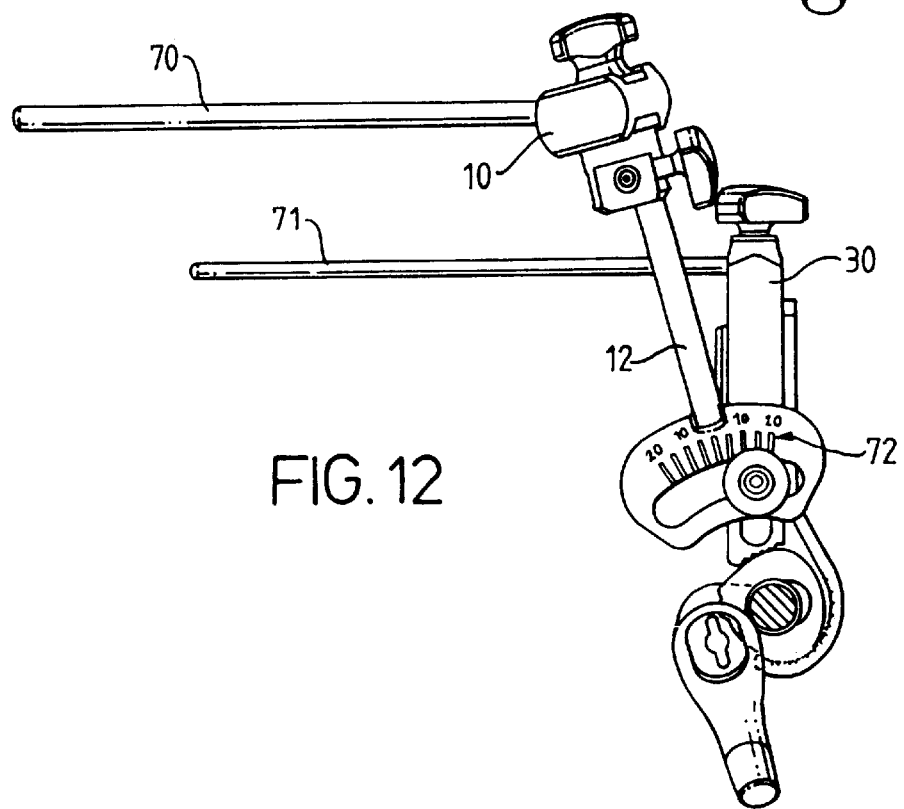
FIG. 12 is a similar view to FIG. 11 with the support element in a second aligned position.

Using the visual indicator guides the apparatus is placed in position with the clamp positioned perpendicular to the 90° knee flexion plane. This is the first position of the anteversion at 0° and this is shown in FIG. 11. In FIG. 12 the L-shaped frame 10 has been rotated until the visual indicator guides 70, 71 are parallel. In this position the frame 10 has been rotated through 15° in relation to the clamp 30. Thus, the neck axis is parallel to the axis of the frame 10 and the rotation of the frame has thus created an angle between the clamp and the frame which is the anteversion angle. The exact angle of anteversion can be read from a scale indicated by reference numeral 72 provided on the bracket 12.

The standard value of anteversion is 15° and this can be used as a datum when setting up the apparatus.

Figure 13:
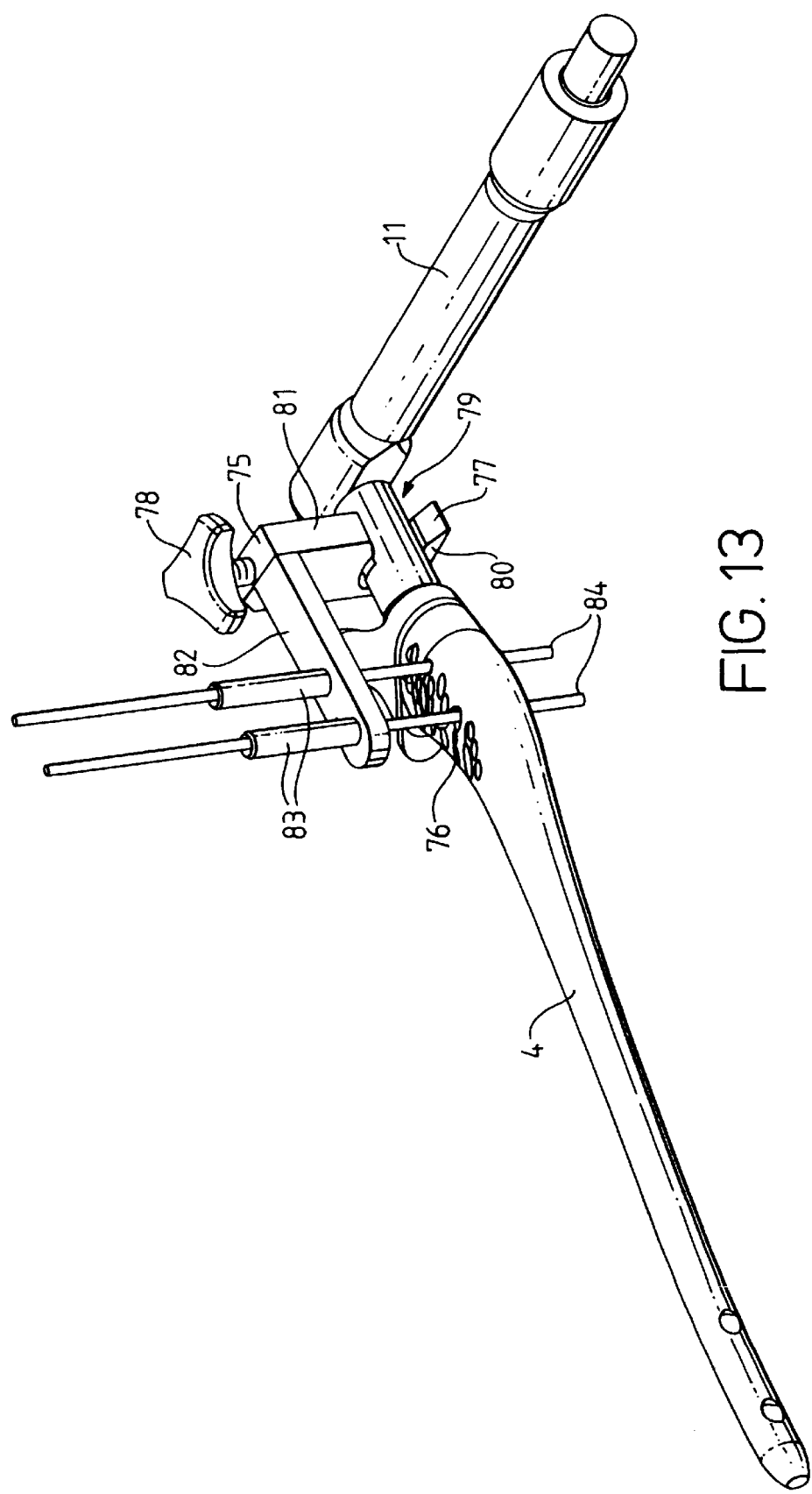
FIG. 13 is an isometric view showing a drill guide which can be clamped into position to enable holes to be made through the bone and soft tissue T when it has been folded back into position on the femur.

When the "window" is closed it is necessary to fold the soft tissue and bone which has previously been folded back to provide the window back into position and locate it around the installed prosthesis. FIG. 13 shows how a proximal drill guide 75 can be provided to guide drills through the folded back "flap" and to enable the drills to line up with the pre-arranged holes 76 provided on the proximal part of prosthesis 4. This device is in the form of an open jawed clamping block 77 which is provided with a tightening screw 78 which passes through a threaded bore (not shown) in the block to extend into the gap 79 provided between a lower clamping jaw 80 and an upper clamping jaw 81. The clamping block 77 carries an arm 82 which supports a pair of drill guides 83.

As will be seen from FIG. 13 the prosthesis is provided with a series of openings 76. With the prosthesis in position in the support element 1 and held by second arm 11 clamping block 77 is placed in position and the drill guides are aligned by the use of guide rods or drills 84. With the drill guides now aligned with the openings 76 the clamping screw 78 is tightened to lock the clamping block in position. The rods or drills 84 can now be removed, the "window" is closed and the drill guides employed to guide the drill or drills to make openings in the flap of bone and soft tissue 48. The openings can then be located by passing wire hoops through the openings and suitable locating them thus ensuring that the flap of material is held in place.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A targeting apparatus for use in performing transfemoral osteotomy surgery comprising a support element provided with a drill guide, means for securing the support element to the proximal end of a prosthesis to be implanted, and means to secure the support element to a resectioned femur, and means for adjusting the angular position of the drill guide in relation to the resectioned femur about a proximal-distal axis.

2. The targeting apparatus as claimed in claim 1 wherein the support element includes a connector for connecting to the proximal end of the femoral prosthesis.

3. The targeting apparatus as claimed in claim 1 further including means to indicate the angular position of the drill guide relative to the resectioned femur.

4. The targeting apparatus as claimed in claim 2 further including means for adjusting the position of the support element to accommodate alternative leg lengths.

5. The targeting apparatus as claimed in claim 4 further including means to vary the proximal-distal position of the support element in relation to the prosthesis connector.

6. The targeting apparatus as claimed in claim 4 wherein the drill guide is located at a predetermined proximal-distal position from the connector for connecting to the proximal end of the femoral prosthesis.

7. The targeting apparatus as claimed in claim 1 further including means for locating the drill guide in alternative proximal-distal positions on the support element.

8. The targeting apparatus as claimed in claim 1 wherein two or more drill guides are provided.

9. The targeting apparatus as claimed in claim 1 wherein the means for securing the support element to the resectioned femur comprising in the form of an adjustable open jawed clamp adapted to partially surround the femur with which it is to be used.

10. The targeting apparatus as claimed in claim 1 further including guide means for locating the resectioned proximal end of the femur.

11. The targeting apparatus as claimed in claim 10 wherein said guide means are carried on the femur securing means.

12. The targeting apparatus as claimed in claim 1 wherein the support element comprising an L-shaped frame, one arm of which carries the drill guide and the femur securing means and the other arm carrying the means for securing the support element to the femoral prosthesis which is to be implanted.

13. The targeting apparatus as claimed in claim 12 wherein the femur securing means are connected to the L-shaped frame by an adjustable bracket which can be adjusted in proximal-distal directions on the frame and in relation to which the femur securing means can be angularly adjusted about a proximal-distal axis.

14. The targeting apparatus as claimed in claim 13 wherein said adjustable bracket comprising readily removable from the L-shaped frame.

15. The targeting apparatus as claimed in claim 1 wherein the femur securing means includes means for adjusting and clamping the securing means according to the femur diameter.

16. The targeting apparatus as claimed in claim 1 wherein the means for securing the support element to the resectioned femur includes a universal joint.

17. The targeting apparatus as claimed in claim 1 further including a drill guide for drilling openings through the bone and soft tissue when it has been folded back into position at the proximal end of the femur.

18. An instrument for locating screw or pin holes in an orthopedic device implanted in a long bone comprising:

a generally L-shaped frame having a first arm coupled to the device and a second arm extending in a direction generally parallel to a longitudinal axis of the long bone, said second arm including a drill guide;

a bone clamp mounted on the second arm and movable with respect thereto at least in the direction of the longitudinal axis of the bone, said clamp having a bone gripping portion at least partially surrounding said long bone for selectively clamping said bone to said frame.

19. The instrument as set forth in claim 18 wherein said bone clamp is slidably connected to said second arm and includes a clamping element for locking said bone clamp in a selected longitudinal position on said arm.

20. The instrument as set forth in claim 18 wherein said first arm is rotatable about said longitudinal axis.

21. The instrument as set forth in claim 20 wherein an angle indicator is provided to show the angular offset of said second arm and said clamp relative to a plane through the longitudinal axis.

22. The instrument as set forth in claim 21 wherein the angular offset measured is with respect to a medial-lateral plane bisecting a femur.

23. The instrument as set forth in claim 18 wherein said drill guide is a tubular element extending along an axis extending generally perpendicular to the longitudinal axis.

24. The instrument as set forth in claim 23 wherein said drill guide is mounted on said second arm in a manner permitting adjustment of said drill guide along said second arm in a direction parallel to said longitudinal axis.

25. The instrument as set forth in claim 18 wherein said L-shaped frame is coupled to said device for rotation about said longitudinal axis.

26. The instrument as set forth in claim 25 wherein said bone clamp is slidably connected to said second arm and includes a clamping element for locking said bone clamp in a selected longitudinal position on said arm.

27. The instrument as set forth in claim 25 wherein an angle indicator is provided to show the angular offset of said second arm and said clamp relative to a plane containing the longitudinal axis of the long bone.

28. The instrument as set forth in claim 27 wherein the angular offset measured is with respect to the medial-lateral plane bisecting a femur.

29. The instrument as set forth in claim 28 further including visual indicator rods attached to the L-shaped frame.

\* \* \* \* \*

UNITED STATES PATENT AND TRADEMARK OFFICE
CERTIFICATE OF CORRECTION

PATENT NO. : 6,746,453 B2
DATED : June 8, 2004
INVENTOR(S) : Nicolas Delogé et al.

It is certified that error appears in the above-identified patent and that said Letters Patent is hereby corrected as shown below:

Column 2,
Line 2, after "element" insert -- , --.
Line 8, "open jawed" should read -- open-jawed --.

Column 3,
Line 12, after "L" insert -- , --.
Line 20, after "apparatus" insert -- of the --.

Column 5,
Line 45, before "resilient" insert -- a --.
Line 47, "are" should read -- is --.
Line 54, "enable" should read -- enables --.

Column 6,
Line 24, "open jawed" should read -- open-jawed --.
Line 42, "suitable" should read -- suitably --.

Column 7,
Line 18, "comprising in" should read -- comprises --.
Lines 18 and 19, "open jawed" should read -- open-jawed --.
Line 28, "comprising" should read -- comprises the form of --.
Line 40, "comprising" should read -- comprises a bracket --.

Signed and Sealed this

Eighth Day of February, 2005

JON W. DUDAS
*Director of the United States Patent and Trademark Office*